United States Patent [19]
Endelson

[11] Patent Number: 5,787,907
[45] Date of Patent: *Aug. 4, 1998

[54] CARD TYPE DENTAL FLOSS DISPENSER WITH RELEASABLY ADHERED FLOSS COIL

[76] Inventor: Robert A. Endelson, 41 Yates Ave., Atlantic Beach, N.Y. 11509

[*] Notice: The term of this patent shall not extend beyond the expiration date of Pat. No. 5,722,439.

[21] Appl. No.: 877,007

[22] Filed: Jun. 16, 1997

Related U.S. Application Data

[63] Continuation of Ser. No. 607,113, Feb. 26, 1996, Pat. No. 5,722,439.

[51] Int. Cl.⁶ .................................................. A61C 15/00
[52] U.S. Cl. ........................ 132/321; 132/324; 206/63.5
[58] Field of Search .................................. 132/321, 323, 132/324, 326, 327, 328, 329; 206/338, 104, 63.3, 63.5, 813; 433/143

[56] References Cited

U.S. PATENT DOCUMENTS

| | | | |
|---|---|---|---|
| 2,911,318 | 11/1959 | Lerch | 206/813 |
| 4,327,755 | 5/1982 | Endelson | 132/321 |
| 4,630,729 | 12/1986 | Hirt et al. | 206/813 |
| 4,807,752 | 2/1989 | Chodorow | 206/63.5 |
| 4,881,560 | 11/1989 | Blank et al. | 132/324 |
| 5,076,423 | 12/1991 | Russack | 206/63.5 |
| 5,322,077 | 6/1994 | Corella | 132/323 |
| 5,372,251 | 12/1994 | Thompson | 206/63.3 |

*Primary Examiner*—John J. Wilson
*Assistant Examiner*—Philogene Pedro
*Attorney, Agent, or Firm*—Kenneth P. Robinson

[57] ABSTRACT

A dental floss dispenser in a card format formed by a base panel having a shallow well surrounded by a peripheral ridge, and a face panel superposed on the base panel and bonded to the ridge. Adjacent the front end of the face panel are an aperture and a miniature cutting blade. Nested in the well is a supply of dental floss constituted by an unsupported flattened helical coil. The floss filament from which the coil is wound has a starting end at the front of the coil, the filament at the rear of the coil passing internally through the coil to emerge from its front as a pull out lead which is threaded through the aperture in the face panel. The starting end of the coil is bonded to adjacent convolutions and thereby prevent unwinding of the unsupported coil. To obtain a useable length of floss, the user pulls on the lead to partially unwind the coil and then cuts off the length on the blade. The bed of the well and a corresponding area on the inner surface of the top panel are each coated with a layer of pressure-sensitive adhesive which adheres to the convolutions of the nested coil to maintain its position and integrity. The tackiness of the pressure-sensitive adhesive is such that when the lead is pulled out to partially unwind the coil, the floss filament is then released from the adhesive coating layers.

20 Claims, 3 Drawing Sheets

1

CARD TYPE DENTAL FLOSS DISPENSER WITH RELEASABLY ADHERED FLOSS COIL

RELATED APPLICATIONS

This application is a continuation of application Ser. No. 08/607,113, filed Feb. 26, 1996, now U.S. Pat. No. 5,722,439.

BACKGROUND OF THE INVENTION

This invention relates generally to dental floss dispensers, and more particularly to a highly compact floss dispenser in a card format, making it possible to conveniently carry the dispenser in a wallet or elsewhere on the person.

Dental disease is largely due to the accumulation of bacterial plaque on the teeth and gums. This plaque acts to generate acids which attack the teeth and gums, giving rise to tooth decay and caries, and resulting in periodontal disease. The therapeutic value of dental floss to dislodge debris collected between the teeth and to break up colonies of bacteria that gather near the gum line is well established.

Dental floss generally takes the form of a nylon, cotton or other filament of synthetic or natural fibers. Usually, the floss is waxed so that as the floss is extruded through a space between the teeth, its passage is lubricated. The advantage of dental floss is that it can traverse hard-to-reach places between the teeth and under bridges that are otherwise inaccessible to toothbrushes or other dental appliances. While toothpicks are sometimes used rather than dental floss, picks tend to impact debris between the teeth rather than to dislodge the debris.

Good dental hygiene dictates the use of floss after every meal so that food particles lodging between the teeth are not permitted to remain in these sites. Since the typical dental floss container or dispenser cannot be conveniently carried on the person, as a practical matter it is not feasible for most individuals to follow the dictates of good dental practice. Thus while these dispensers may be stored in household bathroom cabinets, an individual who wishes to apply dental floss away from home is faced with the problem of how best to carry a floss container in an inconspicuous manner.

Commercially-available dental floss dispensers are generally of the type disclosed in the Tarrson U.S. Pat. No. 4,162,688. This dispenser includes a box-like container having a reel of dental floss therein which is payed out through a top opening, the container being provided with a cutting blade so that a suitable length of dental floss may be separated from the supply. Because of the three-dimensional bulk of this boxlike dispenser, it cannot be conveniently carried in a jacket pocket or elsewhere on the person.

To overcome the practical drawbacks of existing types of dental floss dispensers, disclosed in the Endelson Pat. No. 4,327,755 is a dispenser in a credit card format, making it feasible to carry the dispenser in a wallet or billfold, or even in a shirt packet without injury to the dispenser.

Because credit cards are currently in widespread use, most commercially available wallets incorporate flat slots or pockets adapted to accommodate credit cards without causing the wallet to bulge. Hence a dental floss dispenser in a credit card format may be stored inconspicuously in a wallet and put to use away from home under circumstances where dental floss is usually not available.

The dental floss dispenser in a credit card format disclosed in the Endelson '755 patent comprises a base panel having a peripheral ridge to define a shallow well within which is nested a supply of dental floss in flattened helical coil form. The leading end of the coil passes out of the well through an aperture and is caught by a lug adjacent edge notch cut in the base panel. Anchored in the well is a blade whose cutting edge is exposed by the notch, whereby when floss is pulled out of the well to provide a usable length, it may then be cut by the blade. The dispenser is completed by a face panel bonded to the ridge to encapsulate the floss supply, the face panel having a corresponding notch.

A serious practical drawback of the dental floss dispenser disclosed in the Endelson '755 patent is that this dispenser is difficult and expensive to assemble. The supply of dental floss which must be deposited in the shallow well is an unsupported flattened coil which tends to fall apart unless carefully handled and this handling greatly complicates the assembly procedure.

To overcome this drawback, the Blank and Endelson Pat. No. 4,881,450 discloses a similar dental floss dispenser in a credit card format in which the flattened floss coil is housed within a plastic pouch. This pouch serves to maintain the integrity of the coil during the assembly process and also when the floss is being pulled out from the coil. Yet the floss dispenser disclosed in the '560 patent suffers from disadvantages, for the insertion of the unsupported flattened floss coil into a pouch does not lend itself to automation. This procedure must be carried out manually, thereby making the production of the dispenser labor-intensive and more expensive. The content of U.S. Pat. Nos. 4,327,755 and 4,881,450 is hereby incorporated by reference herein.

SUMMARY OF THE INVENTION

In view of the foregoing, the main object of this invention is to provide a dental floss dispenser in a card format which retains all of the advantages of similar dispensers disclosed in the '755 and '560 patents, yet overcomes their practical drawbacks whereby a dispenser in accordance with the invention can be assembled more easily and at lower cost and function more effectively than the prior art dispensers.

More particularly, an object of the invention is to provide a dental floss dispenser in a highly compact card format which includes internal coatings of pressure sensitive adhesive to maintain the integrity of the unsupported flattened coil of dental floss stored therein without however interfering with the partial unwinding of this coil when a length of floss is pulled out of the dispenser by its user.

Also an object of the invention is to provide in a dental floss dispenser of the above type an unsupported flattened helical coil of dental floss in which the floss filament from which the coil is wound has a starting end at the front of the coil, which filament at the rear of the coil then passes internally through the coil to emerge as a pull out lead at the front of the coil, the starting end of the filament being bonded to adjacent convolutions to prevent unwinding of the coil, whereby its integrity is maintained.

Yet another object of the invention is to provide a floss dispenser in a card format in which the pull out lead of the coil goes through an aperture in the card adjacent its front end, the card having an end slit leading into the aperture to facilitate entry of the lead into the aperture, which slit is thereafter sealed.

Briefly stated, in a preferred embodiment these objects are attained by a dental floss dispenser in a card format formed by a base panel having a shallow well surrounded by a peripheral ridge, and a face panel superposed on the base panel and bonded to the ridge. The face panel is provided adjacent its front end with an aperture and a miniature cutting blade. Nested in the well is a supply of dental floss constituted by an unsupported flattened helical coil. The floss filament from which the coil is wound has a starting end at the front of the coil, the filament at the rear end of the coil passing internally through the coil to emerge at the front as a pull out lead which is threaded through the aperture in the face panel.

The starting end of the coil is bonded to adjacent convolutions to prevent unwinding of the unsupported coil. To obtain a useable length of floss, the user pulls on the lead to partially unwind the coil and then cuts off the length on the blade. The bed of the well and a corresponding area on the inner surface of the top panel are each coated with a layer of pressure-sensitive adhesive which adheres to the convolutions of the nested coil to maintain its position and integrity. The tackiness of the pressure-sensitive adhesive is such that when the lead is pulled out to partially unwind the coil, the floss filament is then released from the adhesive layer.

BRIEF DESCRIPTION OF DRAWINGS

For a better understanding of the invention as well as other objects and further features thereof, reference is made to the following detailed description to be read in conjunction with the accompanying drawings, wherein.

DESCRIPTION OF INVENTION

Figure 1:
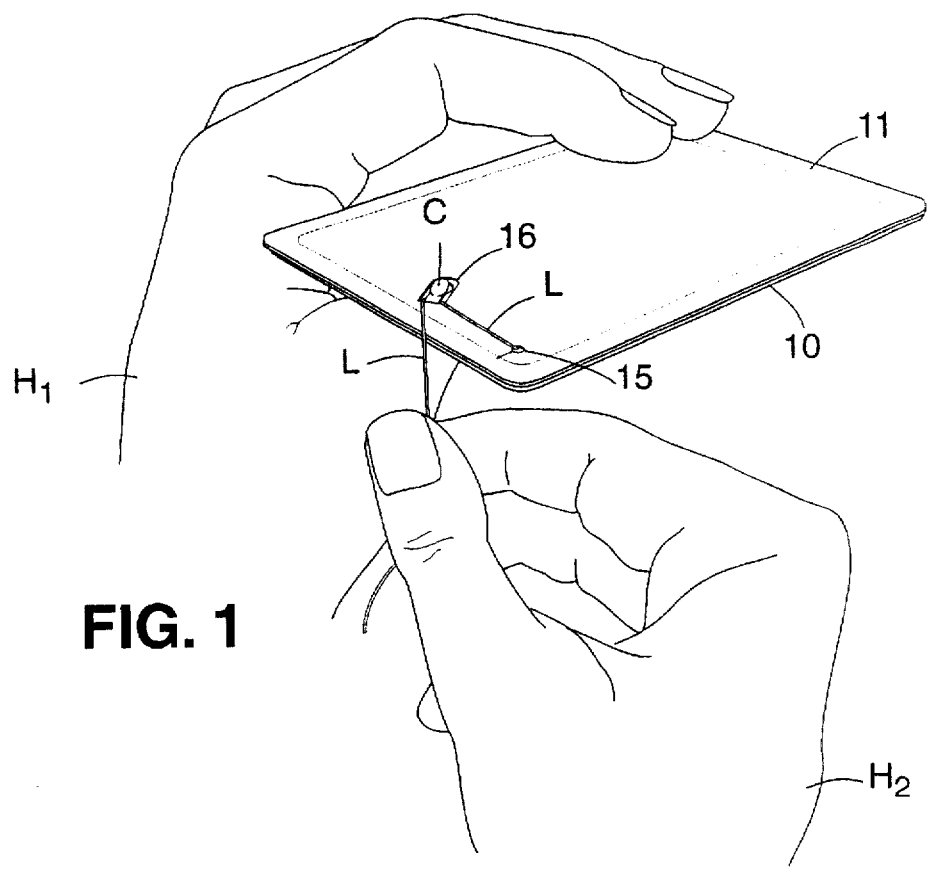
FIG. 1 is a perspective view of a preferred embodiment of a dental floss dispenser in a credit card format in accordance with the invention, the dispenser being held by the user in one hand, while a length of dental floss is pulled out of the dispenser and cut off by the other hand.
Figure 2:
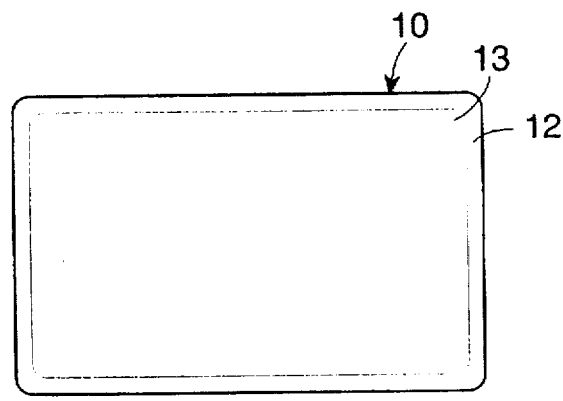
FIG. 2 is a rear view of the dispenser.
Figure 3:
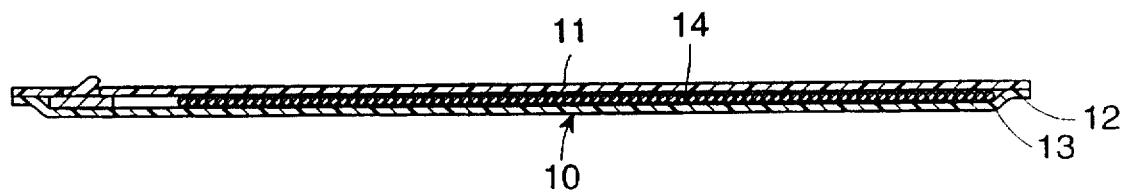
FIG. 3 is a longitudinal section taken through the dispenser.

Referring now to FIGS. 1 to 4, there is shown a dental floss dispenser in accordance with the invention in a credit card format, the dispenser including a rectangular base panel 10 and a complementary face panel 11 superposed thereon. Both panels are preferably fabricated of flexible synthetic plastic material such as polyvinyl chloride or other thermoplastic material. Typical credit card dimensions may be used for the panels, such as 3 ⅜ and 2 ⅛ inches. In practice, the card may be made in different dimensions, and be formed of other materials, such as coated paper or cardboard.

Base panel 10 is depressed to define a shallow rectangular well 13. Within well 13 peripheral ridge 12 is nested a supply of dental floss in the form of a flattened helical coil 14 of waxed dental floss. The preferred technique for fabricating the flattened helical coil is to wind the dental floss filament on a thin metal plate or mandrel whose dimensions are close to those of well 13. In practice the flattened coil may then be pressed with a heated iron which acts to set and sinter the wax constituent of the floss whereby when the mandrel is withdrawn, the unsupported flattened coil retains its shape and may be easily placed within well 13.

Figure 4:
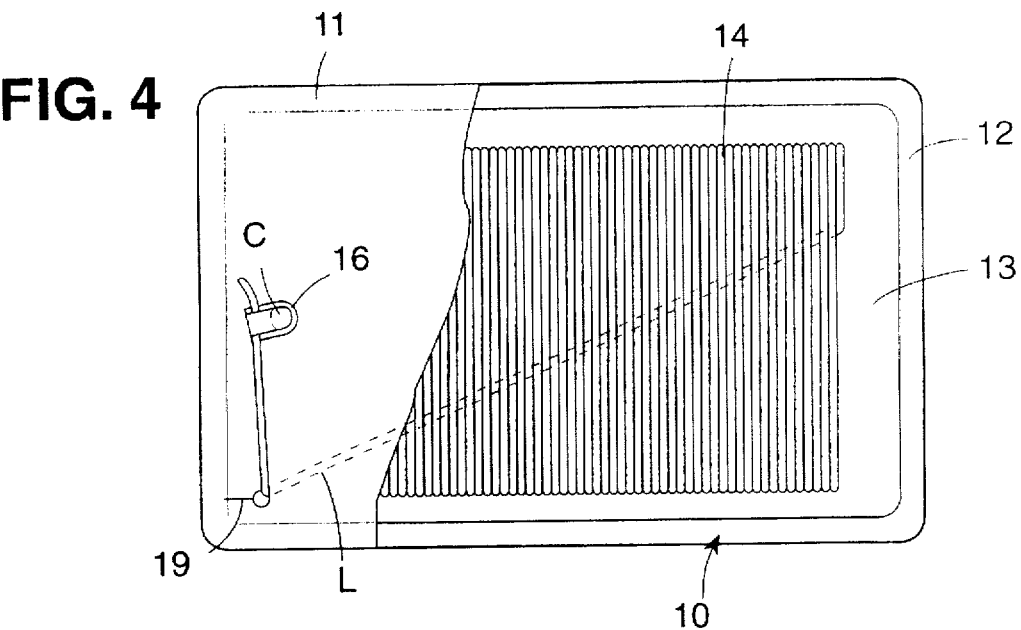
FIG. 4 is a top view of the dispenser with the face panel cut away to expose the flattened floss coil nested in the well of the base panel.
Figure 5:
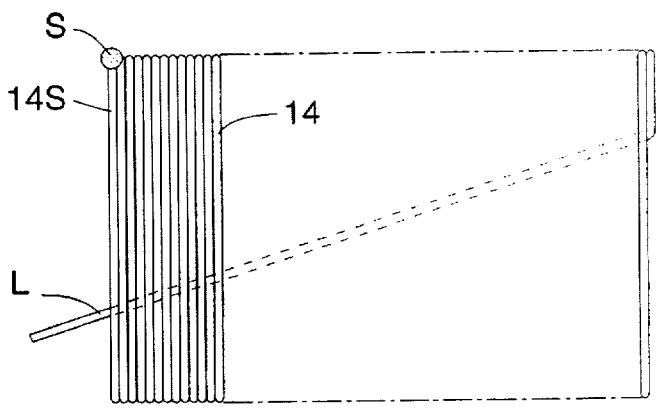
FIG. 5 shows the front end portion of the flattened coil to which a spot of adhesive is applied to prevent unwinding of the coil.
Figures 8, 9, 10:
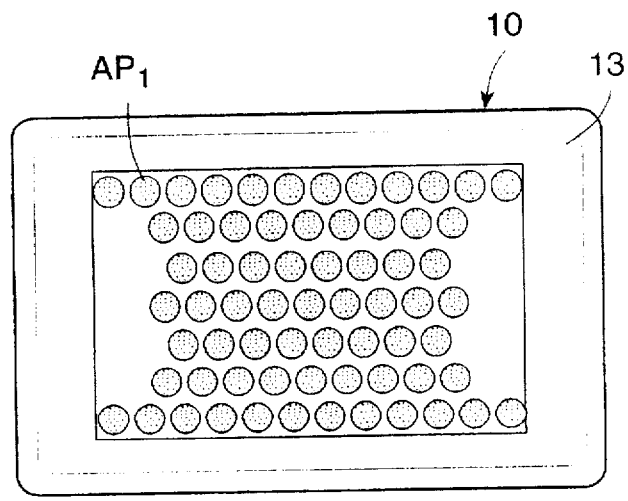
FIG. 8 is a perspective view of the dispenser in which the top panel is raised above the base panel to expose the flattened coil nested in the well of the base panel.
FIG. 9 shows the pattern of the pressure-sensitive adhesive layer coated on the bed of the well in the base panel of the card.
FIG. 10 shows the pattern of the pressure-sensitive adhesive layer coated on a corresponding inner surface of the face panel.

As best seen in FIGS. 4, 5 and 8, flattened coil 14 is constituted by a helically wound floss filament whose starting end 14S is at the front of the coil. This wound filament, when it reaches the rear of the coil, is then passed internally through the coil to emerge from its front as a pull out lead L which when pulled, by a user, proceeds to unwind the coil from the rear toward the front. Thus as the coil is unwound it proceeds to shrink in length. Lead L is threaded through a small aperture 15 adjacent the left corner in face panel 11 at the front end of the card.

Figure 6:
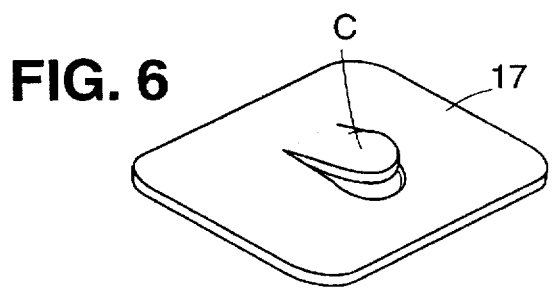
FIG. 6 is a separate view of the cutting blade element of the dispenser.
Figure 7:
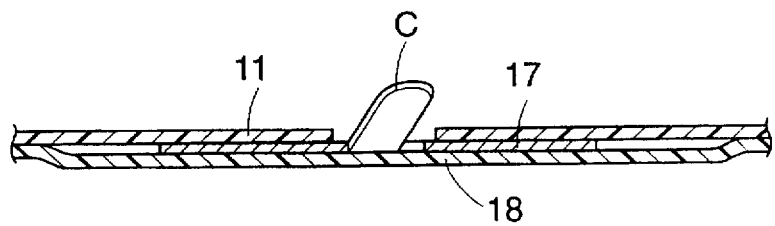
FIG. 7 is a section taken through the face panel of the card showing how the cutting blade element is attached thereto.

Projecting through an opening 16 die cut in the face panel 11 at the center of its front end is a miniature cutting blade $C_1$ that is mounted on a small rectangular plate 17, as shown in FIGS. 6 and 7. Plate 17 is placed against the underside of face panel 11 and secured thereto by a strip 18 of adhesive tape.

When the dispenser is put to use, then as shown in FIG. 1, the user holds the card in one hand $H_1$, and with the fingers of his other hand $H_2$, pulls lead L out of aperture 15 to a desired floss length. He then loops the filament about cutting blade 6 and cuts off this length.

The starting end 14S of the floss filament from which coil 14 is wound, as shown in FIGS. 5 and 8 has a blob (S) of adhesive applied thereto which bonds the starting end to adjacent convolutions of the coil and thereby prevents it from unraveling. The rear of the coil is prevented from unraveling because the filament at the rear end passes through the coil to emerge as the pull out lead L at the front. Hence though the flattened coil is unsupported, it will not fall apart in the course of its transfer from a mandrel to the well in the base panel.

In practice, instead of a blob of adhesive, the starting end 14S of the filament may be thermally bonded to adjacent convolutions to prevent the coil from unraveling.

In order to maintain the integrity of the flattened coil and its proper position in the well 13 of the base panel, the bed of well 13 of the base panel 10, as shown in FIG. 9, is coated with a layer of pressure-sensitive adhesive in a grid-like pattern $AP_1$. This pattern is formed by an array of circular holes which are free of adhesive, so that the adhesive exists only in the network of lands interconnecting the holes.

As shown in FIG. 10, the area of the inner surface of face panel 11 which corresponds to the bed of the well is coated with a layer of pressure-sensitive adhesive in a grid-like pattern $AP_2$ which matches pattern $AP_1$.

When face panel 11 is peripherally bonded to base panel 10 to complete the structure of the dispenser, flattened coil 14 is then encapsulated therein and is thereby sealed to maintain its hygienic condition. Coil 14 is then sandwiched between the adhesive layer $AP_2$ on the inner surface of the face panel and the like adhesive layer $AP_1$ on the bed of the well in the base plate.

The pressure-sensitive adhesive used on these layers is preferably a water-based acrylic composition whose density and tackiness characteristics are such that the adhesive in contact with the convolutions of the flattened coil on both sides thereof lightly adheres thereto to maintain the integrity of the coil and prevent its displacement. But when lead L is pulled out to draw a length of floss filament from the flattened coil, the coil is then partially unwound from the rear thereof to an extent depending on the length pulled out by the user.

As the coil is being partially unwound, the unwinding convolutions thereof in contact with the pressure-sensitive adhesive layers are then released, with no adhesive remaining on these convolutions. Hence the length of floss withdrawn from the dispenser is free of adhesive and is not contaminated thereby. The characteristics of the pressure-sensitive adhesive must be such as to adhere to the convolutions of the nested supply without however sticking to these convolutions when they are pulled away from the adhesive layers.

When the dispenser is being assembled, it is necessary to thread lead L into aperture 15 adjacent one corner at the front end of the face panel 11. To facilitate entry into this aperture, a slit 19 is cut in the face panel that extends from the front end of the panel to aperture 15. In order, therefore, to thread lead L into aperture 15, the lead is drawn edgewise through the slit 19 into the aperture. Since the face panel 11 is formed of thermoplastic material, as is the base panel 10, when the face panel is bonded by heat and pressure to the peripheral ridge 12 of the base panel, this action serves also to seal slit 19.

While a floss dispenser in a card format in accordance with the invention is essentially planar and highly compact, being not much thicker than a standard credit card, it is nevertheless capable of encapsulating a substantial supply of dental floss, and is therefore not quickly exhausted, but may be put to repeated use.

A significant advantage of a dental floss dispenser in accordance with the invention is that it may be personalized and printed under computer control with the names of individuals derived from the computer memory and with the business title of an advertiser, very much in the manner of existing credit cards. Hence such printed floss dispensers may be distributed as advertising premiums that are likely to be treasured by recipients. Or such printed dental floss dispensers may be given away by restaurants and other establishments rather than match books, for there is diminishing interest in the latter, because of the prevalence of disposable butane lighters.

While there has been shown and described a preferred embodiment of a dental floss dispenser in accordance with the invention, it will be appreciated that many changes and modifications may be made therein without, however, departing from the essential spirit of the invention.

Thus instead of nesting the dental floss flattened coil supply in a well in the base panel, the supply may be sandwiched between the base panel and the face panel to occupy a cavity defined between these superposed panels which are peripherally bonded together to enclose the supply.

In a floss dispenser in this format, the supply sandwiched between the panels is adhered thereto by a pressure-sensitive adhesive layer coated on the inner surface of either the base panel or the face panel, or on both panels.

What is claimed is:

1. A dental floss dispenser in a card format, comprising:
   a base panel having a shallow well surrounded by a peripheral ridge;
   a face panel superposed on the base panel and bonded to the ridge to form an interior cavity, said face panel having an aperture;
   an adhesive layer on at least a portion of the surface of said interior cavity, said adhesive layer adapted to provide releasable adhesion to dental floss; and
   a supply of dental floss constituted as an unsupported flattened coil wound of floss, said coil disposed in said interior cavity with convolutions of the coil in contact with said adhesive layer and having a pull out lead extending through said aperture, lengths of said floss being releasable from the adhesive layer when the lead of the coil is pulled.

2. A dental floss dispenser as in claim 1, in which said adhesive layer is positioned on at least a portion of the surface of one of: the shallow well, the undersurface of the face panel, and both said well and said undersurface of the face panel.

3. A dental floss dispenser as in claim 2, in which the adhesive layer comprises a pattern including areas of a pressure-sensitive adhesive and open surface areas which are free of adhesive.

4. A dental floss dispenser as in claim 1, in which the coil comprises a helical coil wound of a floss filament having a starting end at the front of the coil and the filament when reaching the rear of the coil then passing internally through the coil to emerge from the front of the coil as said pullout lead extending through the aperture.

5. A dental floss dispenser as in claim 4, in which the starting end of the filament at the front of the coil is bonded to an adjacent convolution of the coil to prevent the front of the coil from unraveling.

6. A dental floss dispenser as in claim 1, in which the dispenser is of credit card size, with thickness which is a small fraction of length and of width of the dispenser.

7. A dental floss dispenser as in claim 1, additionally including a miniature cutting blade extending through a second aperture in the face panel.

8. A dental floss dispenser as in claim 1, in which the face panel is provided with a slit extending from an edge thereof to said aperture to facilitate entry of the pullout lead into the aperture.

9. A dental floss dispenser as in claim 8, in which after entry of the pullout lead into the aperture, said slit is at least partially bonded closed.

10. A dental floss dispenser as in claim 1, in which the base and face panels comprise portions of thermoplastic sheet material which are thermally bonded together along said peripheral ridge.

11. A dental floss dispenser in a card format, comprising:
    a base panel;
    a face panel fixed in position above the base panel to define an interior cavity between the panels, said face panel having an aperture;
    a surface area adapted to provide releasable adhesion to dental floss, said surface area comprising at least a portion of the surface of said internal cavity, and
    a supply of dental floss constituted as an unsupported flattened coil wound of floss, said coil disposed in said interior cavity with convolutions of the coil in contact with said surface area and having a pullout lead extending through said aperture, lengths of said floss being releasable from adhesion to said surface area when the lead of the coil is pulled.

12. A dental floss dispenser as in claim 11, in which said surface area comprises at least a portion of one of:
    the interior surface of the base panel, the interior surface of the face panel, and the interior surfaces of both of the base and face panels.

13. A dental floss dispenser as in claim 12, in which the surface layer comprises areas of a pressure-sensitive adhesive arranged in a pattern with open surface areas which are free of adhesive.

14. A dental floss dispenser as in claim 11, in which the coil comprises a helical coil wound of a floss filament having a starting end at the front of the coil and the filament when reaching the rear of the coil then passing internally through the coil to emerge from the front of the coil as said pullout lead extending through the aperture.

15. A dental floss dispenser as in claim 14, in which the starting end of the filament at the front of the coil is bonded to an adjacent convolution of the coil to prevent the front of the coil from unraveling.

16. A dental floss dispenser as in claim 11, in which the dispenser is of credit card size, with thickness which is a small fraction of length and of width of the dispenser.

17. A dental floss dispenser as in claim 11, additionally including a miniature cutting blade extending through a second aperture in the face panel.

18. A dental floss dispenser as in claim 11, in which the face panel is provided with a slit extending from an edge thereof to said aperture to facilitate entry of the pullout lead into the aperture.

19. A dental floss dispenser as in claim 11, in which the base and face panels are thermally bonded to form said interior cavity and said slit is at least partially bonded closed.

20. A dental floss dispenser in credit card format, comprising:

a base panel of plastic sheet material formed to provide a shallow well surrounded by a peripheral ridge;

a face panel of planar plastic sheet material superposed on the base panel and bonded to said ridge to form an interior cavity, said face panel having an aperture;

a miniature cutting blade extending through a second aperture in the face panel;

an adhesive layer of pressure-sensitive adhesive positioned on at least a portion of the surface of said interior cavity, said adhesive layer adapted to provide releasable adhesion to dental floss; and a supply of dental floss constituted as an unsupported flattened helical coil wound of a floss filament disposed in said well with convolutions of the coil in contact with said adhesive layer, said filament having a starting end at the front of the coil and the filament when reaching the rear of the coil then passing internally through the coil to emerge from the front of the coil as a pullout lead extending through said aperture, lengths of said floss being releasable from the adhesive layer when the lead of the coil is pulled.

* * * * *